United States Patent
Berry, III et al.

(10) Patent No.: US 6,327,902 B1
(45) Date of Patent: *Dec. 11, 2001

(54) AIR FILTER RESTRICTION INDICATOR GAUGE

(75) Inventors: Charles Henry Berry, III; Gregory Matthew Ferris, both of Cedar Falls, IA (US)

(73) Assignee: Engineered Products Company, Waterloo, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/344,737

(22) Filed: Jun. 25, 1999

(51) Int. Cl.⁷ .................................................. B01D 35/143
(52) U.S. Cl. ..................... 73/119 R; 73/118.1; 116/268; 116/270; 116/DIG. 25; 340/607
(58) Field of Search ............................. 73/118.1, 119 R; 116/200, 268, 270, 276, DIG. 25; 340/438, 606, 607

(56) References Cited

U.S. PATENT DOCUMENTS

| | | |
|---|---|---|
| 2,946,222 | 5/1960 | Husjack . |
| 3,443,365 * | 5/1969 | Lee et al. . |
| 3,465,707 * | 9/1969 | Kashiwaba . |
| 3,594,745 | 7/1971 | Nickels . |
| 3,654,414 | 4/1972 | Kudlaty . |
| 3,696,666 | 10/1972 | Johnson et al. . |
| 3,939,457 | 2/1976 | Nelson . |
| 4,033,733 | 7/1977 | Nelson . |
| 4,171,962 | 10/1979 | Kippel et al. . |
| 4,183,029 | 1/1980 | Isayama et al. . |
| 4,279,162 | 7/1981 | Neill et al. . |
| 4,369,728 | 1/1983 | Nelson . |
| 4,423,751 | 1/1984 | Roettgen . |
| 4,445,456 | 5/1984 | Nelson . |
| 4,688,511 * | 8/1987 | Gerlach et al. . |
| 4,937,557 | 6/1990 | Tucci et al. . |
| 5,092,177 | 3/1992 | Varacca . |
| 5,239,861 | 8/1993 | Fujita et al. . |
| 5,315,875 | 5/1994 | Benedikt et al. . |
| 5,477,731 | 12/1995 | Mouton . |
| 5,774,056 | 6/1998 | Berry, III et al. . |
| 5,850,183 * | 12/1998 | Berry, III . |
| 6,161,417 * | 12/2000 | Nepsund . |
| 6,268,791 * | 7/2001 | Ferris . |

FOREIGN PATENT DOCUMENTS

| | | |
|---|---|---|
| 43 15 577 A1 | 12/1993 | (DE) . |
| 0 728 936 A2 | 12/1995 | (EP) . |
| WO 97/06363 | 2/1997 | (WO) . |

* cited by examiner

*Primary Examiner*—Eric S. McCall
(74) *Attorney, Agent, or Firm*—Oppenheimer Wolff & Donnelly LLP

(57) ABSTRACT

A low cost air filter restriction indicator gauge for use in conjunction with an internal combustion engine can be achieved by both simplifying individual part configuration and reducing overall part count. More specifically, a simplified design can be achieved by utilizing a one piece base cap which includes a locking extension and reset button integral therewith. By having this part injection moldable, it is easy to fabricate and lower in cost as a complex locking pin assembly can be eliminated. Further, the low cost device can be further enhanced by providing a two color visual indicator which displays one color when the device is in its reset position and a second color when the device is in its locked or set position.

17 Claims, 7 Drawing Sheets

AIR FILTER RESTRICTION INDICATOR GAUGE

BACKGROUND OF THE INVENTION

The present invention relates to a gauge for monitoring the filtering performance of a vehicle filter. More specifically, the present invention relates to a low cost, simplified gauge for helping vehicle owners determine whether their air filter needs replacement.

Air filter restriction gauges are used in connection with an air filter for internal combustion engines. These devices typically sense the level of airflow restriction, and provide an indication of this restriction level by providing some type of display. When the air filter has become so loaded with contaminants that the supply of air required by the engine for its operating efficiency is not being drawn through the filter, the gauge will indicate this and thus alert the operator that the filter requires cleaning or replacement. Some existing devices will also lock themselves in various positions to provide a continuous indication as to how much useful life remains in the air filter before it should be cleaned or changed.

The use of a gauge to monitor the filtering ability of a vehicle's air filter is known in the art. Earlier patents in this area include U.S. Pat. No. 4,369,728, issued to Nelson on Jan. 25, 1983, and U.S. Pat. No. 4,445,456, issued to Nelson on May 1, 1984. These devices provided an incremental visual display to the users or maintenance personnel.

Air filter restriction indicator gauges have been available for quite some time. Initially, these indicator gauges were simply a single stage type gauge where a warning button would pop-up once a predetermined restriction level was achieved. The pop-up type gauges were not believed to be reliable and typically not trusted. The design of these gauges was complex and prone to many variations in performance. Also, this pop-up type gauge was difficult to manufacture due to the number of parts required and the intricacies of their assembly.

Additionally, prior art indicators have not always been easy to fully reset, sometimes resulting in a gauge that may give a false, premature signal that an air filter requires replacement. These false signals result in unnecessary filter maintenance—precisely what the gauge is intended to avoid.

In order to accommodate the locking features of prior indicator gauges, previous systems have required fairly involved and complex lock up mechanisms. Often these gauges comprise separate hinged locking pins which must be appropriately attached and aligned within the gauge. As expected, this has provided a manufacturing challenge to accomplish this necessary alignment. As can be easily appreciated, these types of structures also involve additional steps to assemble.

As most gauges have a locking feature so as to indicate that the predetermined vacuum level has been achieved, it is also necessary to provide reset capabilities. This provides additional design challenges when the lock pin is configured. More specifically, the lock pin must be accessible from the back side. Ideally, the button is depressed to unlock the mechanism. This resetting feature of previous designs which have a separate hinged locking pin structure makes the gauges more complex and costly to fabricate.

SUMMARY OF THE INVENTION

The present invention provides a more cost competitive product by dramatically simplifying the base cap design. In general, a one piece base cap is provided which includes an integral reset button and lock up extension, thus eliminating the need for a separate lock pin assembly. The part is specifically designed to be injection moldable while also providing the necessary functionality. A low cost economical restriction indicator gauge is thus provided with a lower part count and a simplified method of manufacturing.

The restriction indicator gauge is used in internal combustion engines for helping owners, maintenance personnel and operators determine when new air filters are required. The gauge of this invention is attached to the engine between the filter and the air intake and monitors the air pressure sign existing at that point. As is clearly understood, the pressure is likely to be a vacuum as the intake is pulling air into the engine. Once the gauge experiences a vacuum signal of a predetermined level, the gauge will "set," thus indicating that the vacuum is undesirably high. This then provides an indication that the air filter must be changed.

The gauge of the present invention includes a housing which has an inlet in communication with the air intake system. Within the housing is attached a flexible diaphragm, forming an enclosed chamber inside the housing. As the flexible diaphragm is exposed to the vacuum signal, the diaphragm may be caused to move depending on the level of the vacuum. Attached to the flexible diaphragm is a sealing ring and alignment cup which help to maintain a seal between the internal chamber and the remainder of the gauge. The gauge further has a base cap which is attached to the housing such that it is on an opposite side of the diaphragm from the internal chamber. An integral locking extension in the base cap interacts with the sealing ring to provide the necessary lock up function.

The base cap is a single piece molded structure which is attached to the housing by a snap fit connection. This base cap includes the aforementioned lock pin extension as an integral part thereof. The integral lock pin extension eliminates the need for separate lock pin mechanisms which have been used in prior gauges. As is necessary, this lock pin extension is formed into a hinged reset button structure. As such, the reset button is easily depressed causing appropriate movement of the lock pin to unlock the gauge.

The hinge reset button structure of the present invention is again an integral part of the base cap. The base cap continues to be a single one-piece structure which is easily injection molded. The base cap however is specifically designed to avoid many problems typical to molded plastic parts. That is, the base cap is specifically designed to avoid the "setting" phenomena that may occur. The setting problem is avoided by specifically designing the base cap so that its hinging portion will not be permanently bent into an undesired configuration. By having the lock pin extension appropriately cooperate with other elements of the gauge, the reset button and the hinging element are held in their rest position for a majority of the time. As such, the only time the hinging element is stressed is when the gauge is reset. Consequently, it is highly unlikely that the gauge hinge will take on a set.

The housing additionally includes a clear window which is appropriately positioned to provide an appropriate visual indication. In operation, the vacuum signal creates forces on the flexible diaphragm. These forces can cause the flexible diaphragm to move toward the top of the housing. This causes related movement of the alignment cup and sealing ring. The alignment cup and housing window are specifically designed so that the alignment cup will become increasingly visible as it moves towards the top of the housing. Once the predetermined vacuum signal has been reached and the gauge is "set," the alignment cup then becomes fully visible in the window. This is accomplished by having the lock pin extension interact with the sealing ring once a desired range of movement has been achieved.

By having the base cap be a single molded part, the parts count for the gauge is reduced. Further, the locking mechanism is greatly simplified, which provides for a product which is much easier to manufacture.

It is an object of the present invention to provide a low cost restriction indicator gauge having a simplified design which is easy to manufacture.

It is another object of the present invention to provide a reliable indicator gauge which will display indications that the gauge has experienced one or more predetermined vacuum levels at its input. This can then signal maintenance personnel that a new air filter is required.

It is yet another object of the present invention to provide an indicator which is highly visible to service personnel. This indicator will include brightly colored portions which are brought into view once the predetermined vacuum levels have been achieved.

It is a further object of the present invention to provide a simplified low cost gauge which includes a single piece molded base cap which is easily attached to the gauge. This single piece base cap includes the components necessary to provide lock up and reset capabilities to the present invention.

It is another object of the present invention which utilizes a single piece molded base cap which avoids the setting problem which is common to many molded parts. This allows the use of a molded plastic hinge element which will remain in its normal or natural configuration.

It is an additional object of the present invention to provide a lock up gauge which locks into an appropriate configuration upon experiencing a predetermined vacuum signal. The device provides one or more locking positions to display appropriate indications to the users.

BRIEF DESCRIPTION OF THE DRAWINGS

Further objects and advantages of the present invention can be seen by referring to the following detailed description, and the drawings in which.

DETAILED DESCRIPTION OF PREFERRED EMBODIMENTS

A restriction indicator gauge is useful in providing a reliable indication of an air filter's performance. By having this restriction indicator attached to the air intake system of an internal combustion engine, owners and/or maintenance personnel can have a reliable indication regarding the operating condition of their air filters. Consequently, air filters are less likely to be changed prematurely thus saving costs for the engine owners.

Figure 1:
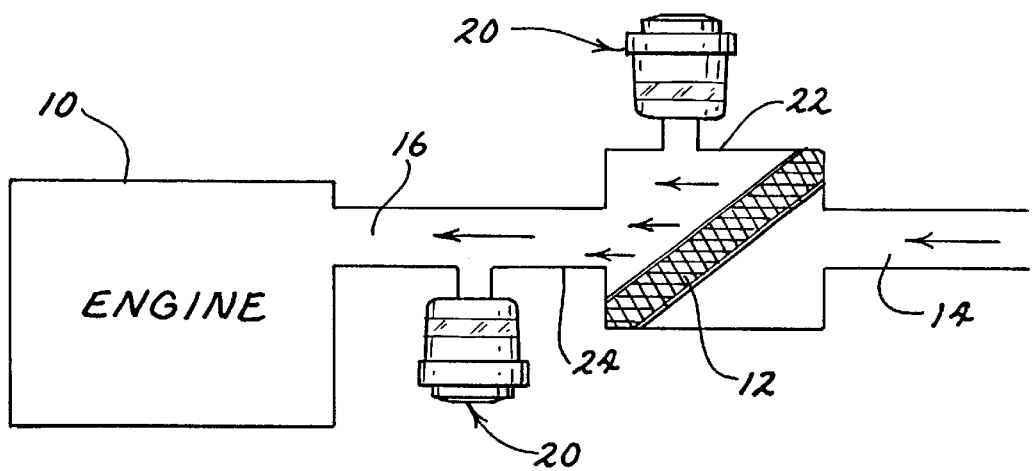
FIG. 1 is a schematic drawing showing a simplified air intake system of an internal combustion engine.

Referring to FIG. 1, there is shown a conceptual diagram of an engine's intake system. As is understood by those skilled in the art, the engine 10 draws air through a filter 12. More specifically, air is drawn into a filter intake 14, through filter 12, and then on to the actual engine air intake 16.

Attached to air intake 16, downstream from filter 12, is shown the restriction indicator gauge 20 of the present invention. Actually, two restriction indicator gauges 20 are shown in alternative locations, a first on the filter housing 22, and a second attached to intake coupling 24. Either location is acceptable as the same pressure or vacuum signal can be measured from either location.

Figure 2:
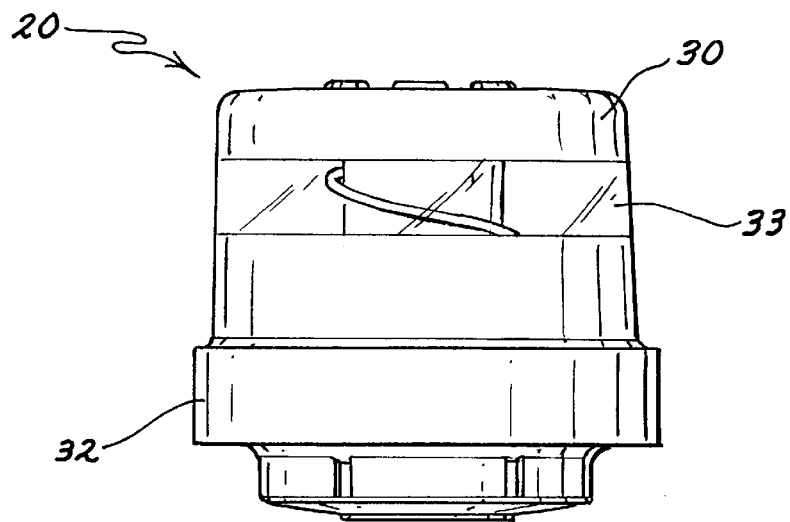
FIG. 2 is a side view of the restriction indicator gauge of the present invention.

FIG. 2 shows a side view of restriction indicator gauge 20. As can be seen, restriction indicator gauge 20 includes a housing 30 and a coupled base cap 32. Also shown in FIG. 2, housing 30 includes a window 33 for viewing a visual indicator.

Figure 3:
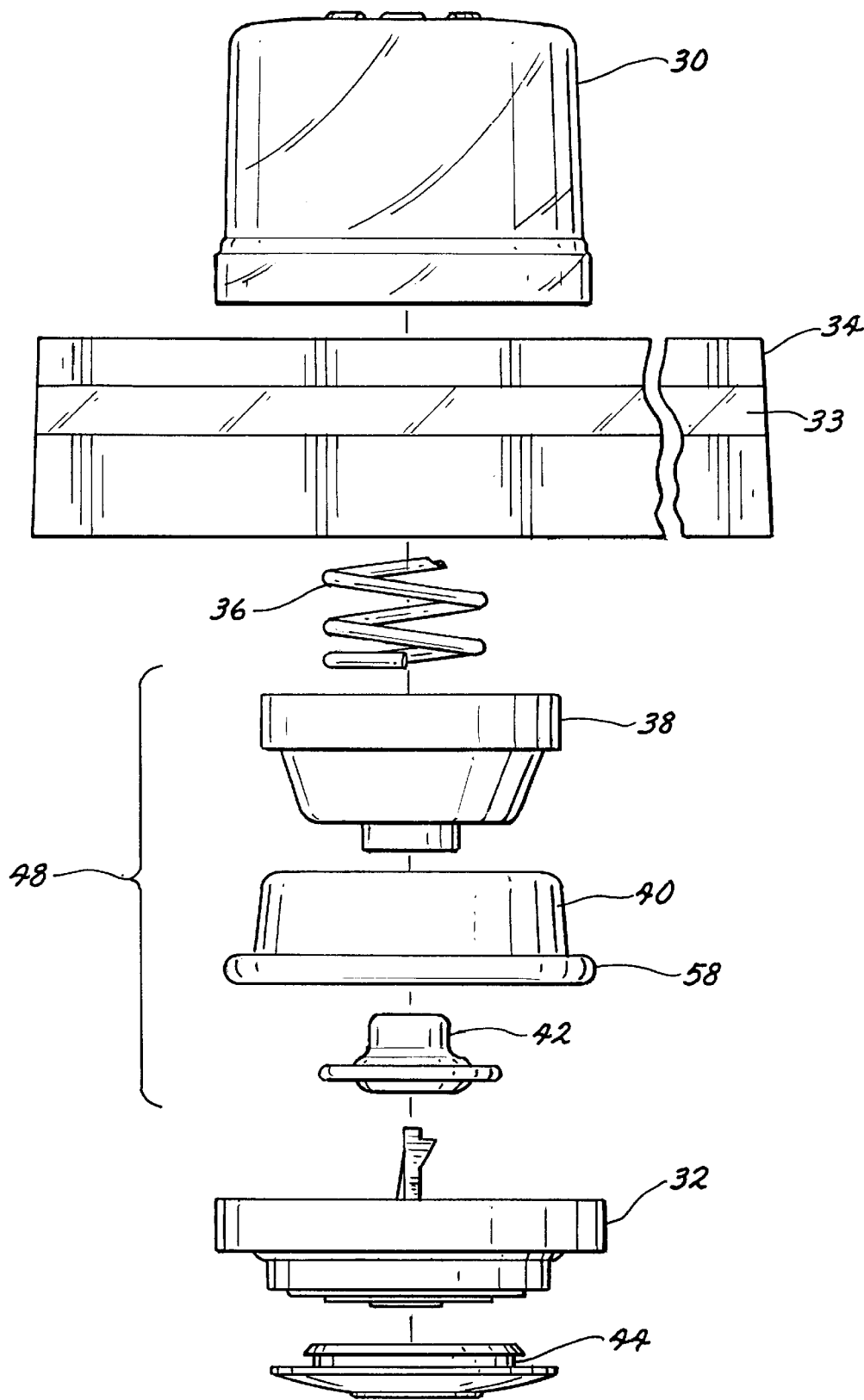
FIG. 3 is an exploded view showing the components of the restriction indicator gauge.

Referring now to FIG. 3, the internal components making up restriction indicator gauge are shown in an exploded format. As previously mentioned, restriction indicator 20 includes housing 30 and base cap 32. These are the two major components which form the external structure of the gauge. Further included within the gauge are a label 34, a calibration spring 36 an indicator cup 38 (or alignment cup 38), a flexible diaphragm 40, a lock ring 42, and a reset cover 44. In operation, indicator cup 38, flexible diaphragm 40, and lock ring 42 all make up a diaphragm assembly 48 which is movable within housing 30.

Figure 4:
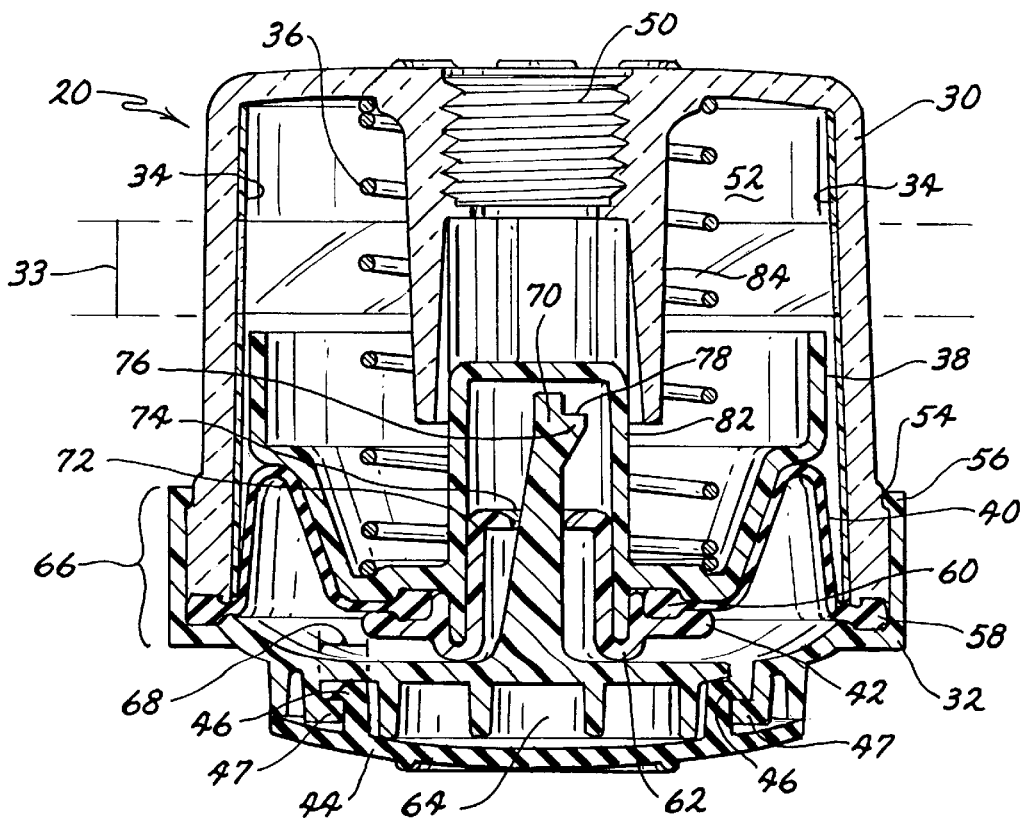
FIG. 4 is a cross sectional diagram of the restriction indicator gauge in its rest or reset position.

Referring now to FIG. 4, the relationship of the various components, when assembled, can be more easily seen. FIG. 4 provides a cross sectional view of restriction indicator gauge 20 in its reset or rest position. Housing 30 has an inlet 50 at one end thereof. Inlet 50 is configured for attachment to the air intake system, and consequently allows the desired pressure or vacuum signal to enter an internal chamber 52 within housing 30.

With general reference back to FIG. 1, it will be understood that there are many different ways to attach switch gauge 20 to engine air intake 16. For example, a threaded attachment could extend outwardly from air intake 16 which would accommodate attachment of switch gauge 20 thereto. Further, a bayonet-type mount could be used which again would attach directly to air intake 16. Generally speaking, any mechanism could be used which would physically connect switch gauge 20 so that inlet 50 is exposed to the pressure signals within the air intake 16.

Housing 30 is attached to base cap 32 via a snap fitting. This snap fitting is accomplished by appropriate grooves 54 in housing 30 and related ridges 56 in base cap 32. This snap fitting between housing 30 and base cap 32 also captures an exterior edge 58 of flexible diaphragm 40. The interface is specifically configured to form an air tight seal between flexible diaphragm 40 and housing 30.

Also attached to flexible diaphragm 40 are indicator cup 38 and lock ring 42. An internal edge 60 of flexible diaphragm 40 is captured between lock ring 42 and indicator cup 38. Indicator cup 38 and lock ring 42 are specifically designed to interlock with one another, and form a seal with flexible diaphragm 40. Indicator cup 38 is configured to be within housing internal chamber 52 whereas lock ring 42 is positioned on the opposite side of flexible diaphragm 40. Thus, lock ring 42 is not contained within internal chamber 52.

Also situated within internal chamber 52 is calibration spring 36. Calibration spring 36 is in contact with housing 30 at one end, and indicator cup 38 at another end. As is obvious from this positioning, calibration spring 36 is designed to bias indicator cup 38 away from the top of housing 30. In FIG. 4, indicator cup 38 and lock ring 42 are positioned in their reset or rest positions. As can be seen, a lower extension 62 of lock ring 42 is in contact with base cap 32. Diaphragm assembly 48 (again, including indicator cup 38, flexible diaphragm 40, and lock ring 42) will be held in this position by calibration spring 36 until additional forces are created to counteract the force of calibration spring 36.

Figure 7:
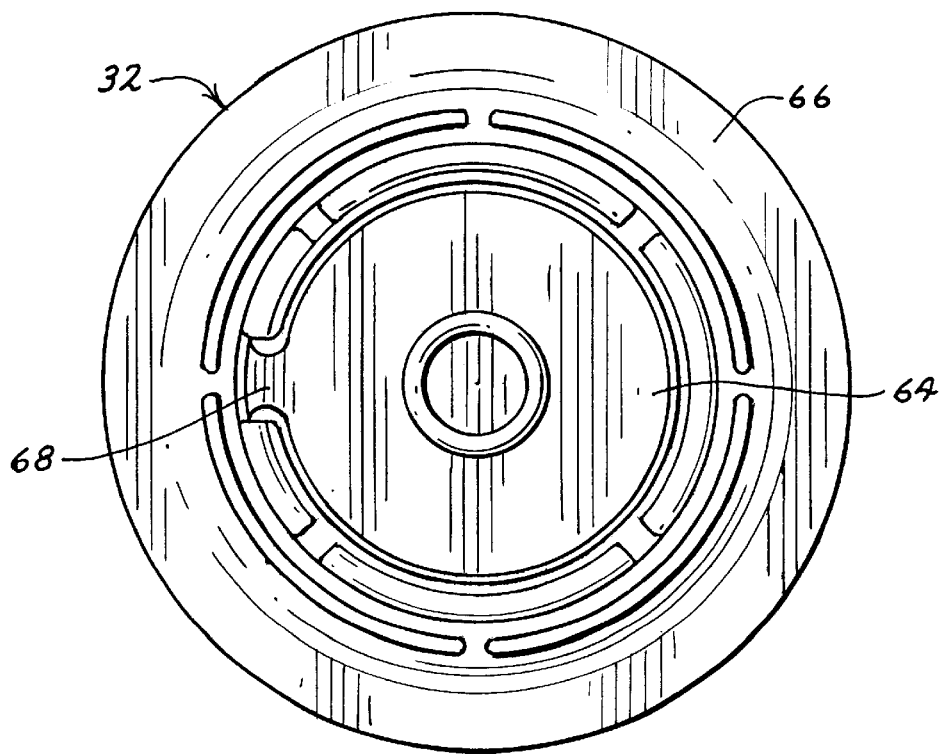
FIG. 7 is a bottom view of the restriction indicator gauge with the reset cover removed.

Base cap 32 is positioned immediately adjacent lock ring 42, and at times, in contact therewith. Base cap 32 includes a button portion 64 and an annular outer portion 66. A hinge element 68 connects button portion 64 and annular outer portion 66 to one another. Referring to FIG. 7, there is shown a bottom view of base cap 32 (with base cap 32 removed), where button portion 64, annular outer portion 66, and hinge element 68 can be more easily seen.

Base cap 32 also includes an integral locking extension 70 which extends upwardly from button portion 64. Locking extension 70 is specifically configured to interact with an upper portion 72 of lock ring 42. This upper portion 72 includes an opening or hole 74, through which locking extension 70 extends. When diaphragm assembly 48 is in its reset position, as shown in FIG. 4, locking extension 70 extends upwardly through lock ring opening 74 and is situated immediately below indicator cup 38. Locking extension 70 includes a ramped, notched portion 76 at an upper end thereof. This ramped, notched portion 76 will interact with lock ring 42 when lock ring 42 is moved upwardly.

Figure 9:
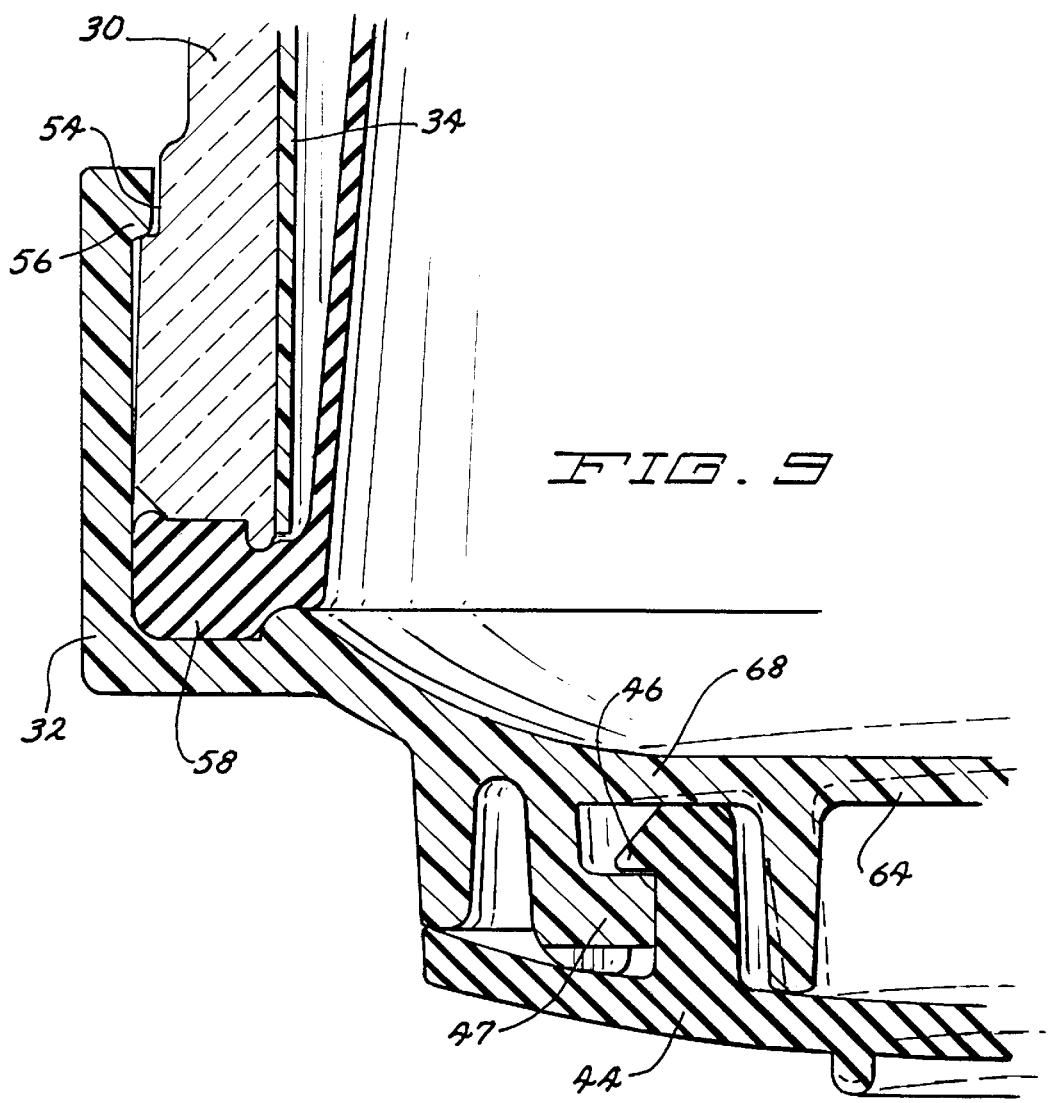
FIG. 9 is an enlarged partial sectional view of the restriction indicator gauge showing the connection between the housing and base cap.

Reset cover 44 is configured to snap into base cap 32. Outwardly extending extensions 46 of reset cover 44 are configured to interact with lips 47 and base cap 32. More specifically, locking tab 46 of reset cover 44 is shown to insert and interlock with structural tab 47. Consequently, reset cover 44 is held in place immediately beneath button portion 64. As previously mentioned, base cap 32 provides a snap fit attachment mechanism to housing 30. Referring to FIG. 9, an enlarged portion of this joint can be seen. More specifically, outer edge 58 of flexible diaphragm 40 is shown sandwiched between base cap 32 and housing 30. Also situated immediately adjacent the inner wall of housing 30 is shown label 34.

Referring to FIG. 9, the hinging operation of the present invention is also shown. Specifically, button portion 64 of base cap 32 is shown in two positions in FIG. 9. First, shown in cross sectional form, button portion 64 is in its natural or rest position. Alternatively, shown in phantom outline, button portion 64 has been moved to a depressed position such that a portion has rotated about hinge portion 68.

As previously mentioned, the engine to which restriction indicator gauge 20 is attached creates a vacuum signal downstream from the air filter. This vacuum signal is translated to internal chamber 52 via housing inlet 50. As internal chamber 52 is an air-tight enclosure, this vacuum signal creates a force on all walls thereof, including diaphragm assembly 48. Because flexible diaphragm 40 is allowed to freely move, the vacuum signal creates a translational force which urges diaphragm assembly 48 upward. This translational force opposes calibration spring 52 to create a controlled movement of diaphragm assembly 48. As the vacuum signal increases, the force also increases, thus causing compression of calibration spring 36.

Figure 5:
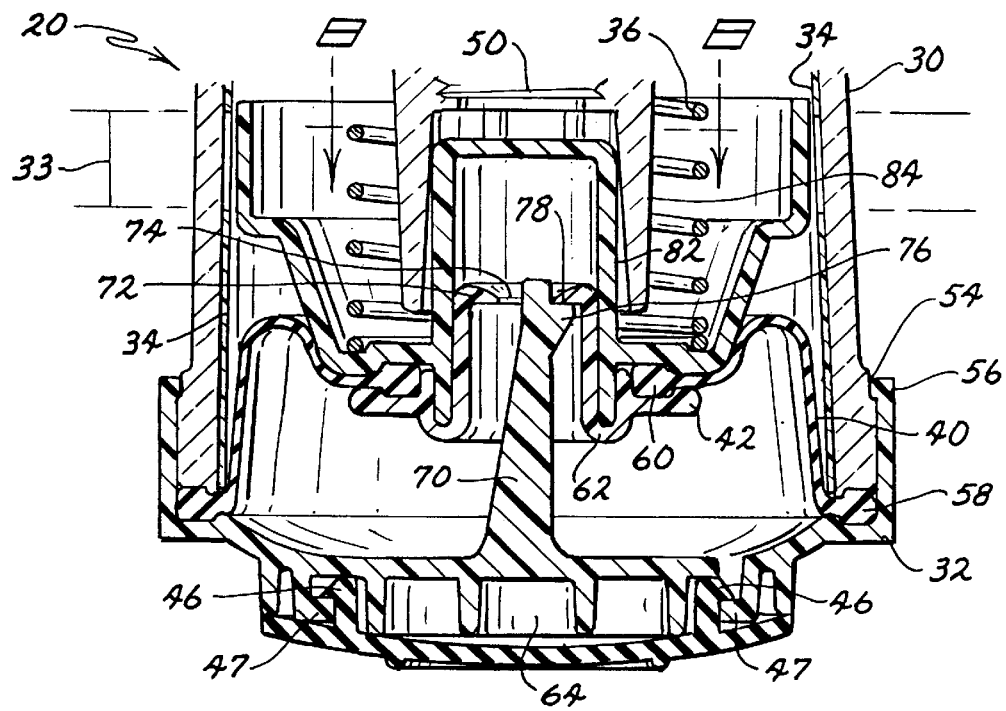
FIG. 5 is a partial cross sectional diagram of the restriction indicator gauge in its locked or set position.

Referring now to FIG. 5, restriction indicator gauge 20 is shown after it has reached a predetermined vacuum signal level. The components are chosen so that this predetermined vacuum signal level will produce a very predictable range of motion for diaphragm assembly 48. As can be seen in FIG. 5, diaphragm assembly 48 has moved to a position where it is now locked in its set or locked position. This locking is accomplished by having ramped notch 76 retain lock ring 42 in the set position. Stated alternatively, the annular surface surrounding lock ring opening 74 is in direct contact with an upper shelf portion 78 of ramp notch 76.

In order to reset restriction indicator gauge 20, the locking or holding relationship between locking extension 70 and lock ring 42 must be disturbed. To accomplish this, button portion 64 of base cap 32 is depressed, causing a related lateral movement of locking extension 70.

Figure 6:
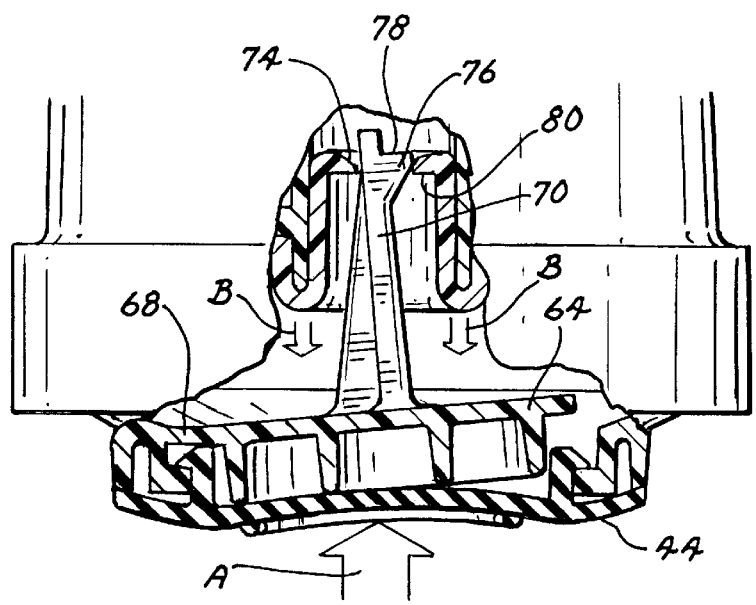
FIG. 6 is a partial sectional diagram of the restriction indicator gauge illustrating the operation of the reset button.

Referring now to FIG. 6, button portion 64 is shown in its depressed orientation. More specifically, a force is applied to reset cover 44 in the direction of arrow A. This causes a hinging movement of button portion 64 about hinge element 68. This hinging action causes locking extension 70 to move laterally, thus sliding upper shelf portion 78 out from the holding surface 80 of lock ring 42.

As previously mentioned, calibration spring 36 biases diaphragm assembly 48 away from the upper portion of housing 30. Consequently, when upper shelf portion 78 of locking extension 70 is pulled out from beneath lock ring 42, calibration spring 36 causes motion in the direction of arrow B. Lock ring 42 can then proceed downwardly in this direction until it contacts button portion 64 (provided no counteracting vacuum signal is present in internal chamber 52).

Referring now to FIG. 14, the functional action of button portion 64 is shown. More specifically, FIG. 14 shows how button portion 64 reacts to various forces. In each case, locking extension 70 is designed to extend upwardly from the button portion 64. This entire structure of locking extension 70 and button portion 64 is attached to annular outer portion 66 via hinge element 68. In each case, the hinge produces a desired reaction to forces presented by various elements.

Figure 14A:
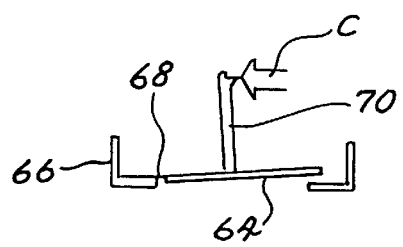
FIG. 14 is a schematic diagram of the base cap button portion.

Referring now specifically to FIG. 14A, when a lateral force is presented to locking extension 70 in the direction shown by arrow C, button portion 64 and locking extension 70 both rotate about hinge portion 68. This force would be presented to locking extension 70 in this manner as diaphragm assembly 48 travels upwardly. That is, as the vacuum signal within internal chamber 52 is increased, force is presented via flexible diaphragm 40 to the lock ring 42.

Lock ring 42 slides along locking extension 70 until reaching ramp notch 76. Due to the configuration of ramp notch 76, a lateral force is then presented to locking extension 70 in the direction of arrow C. This force produces the aforementioned desired reaction of causing button 64 (and locking extension 70) to rotate about hinge element 68.

Figure 14B:
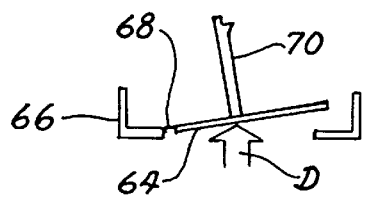

Referring to FIG. 14B, the reaction of button portion 64 is shown to an upward force presented from below in the direction of arrow D. Force in the direction of D represents the typical reset force which would be applied by the user to reset the restriction indicator gauge 20. Once again, the desired rotation motion about hinge element 68 is shown.

Figure 14C:
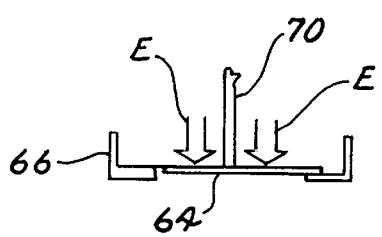

Referring now to FIG. 14C, button 64 is now exposed to a downward force in the direction of arrows E. As can be seen, this downward force causes button portion 64 to be moved back to its rest position. The force in direction of E represents that force that would be presented by calibration spring 36 as it biases diaphragm assembly 48 back down into contact with button portion 64. Specifically, this force would be presented by lock ring 42 as it contacts button portion 64.

Figure 14D:
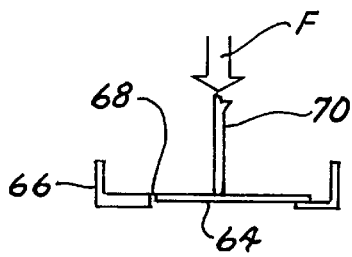

Lastly, FIG. 14D shows a force represented by arrow F in a downward direction which is applied to the top of locking extension 70. This again moves button portion 64 back into its rest position. This force would exist when a portion of indicator cup 38 is in contact with the top of locking extension 70.

As can be appreciated, the different forces presented in FIG. 14 represent those which would be typically encountered during in a normal operating cycle.

Figure 8:
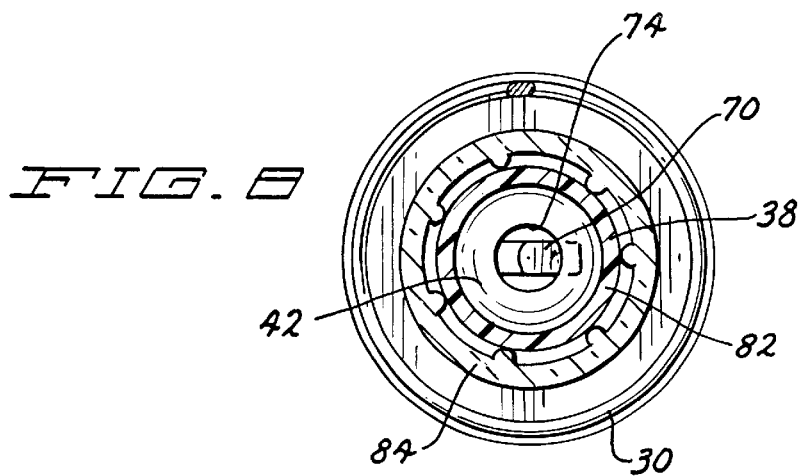
FIG. 8 is a partial sectional view along section line 8—8 as shown in FIG. 5.

Referring now to FIG. 8 there shown a top cross sectional view consistent with section lines 8—8 of FIG. 5. Specifically, this figure shows the top surface of lock ring 42 and lock ring opening 74 situated therein. Locking extension 70 extends at least partially through lock ring opening 74. As can be seen by comparing FIG. 5, this sectional diagram is shown with diaphragm assembly 48 in its locked position.

The cooperation between base cap 32 and diaphragm assembly 48 specifically accommodates the use of a single base cap design. As is well known by those familiar with plastic moldings, a problem or complication exists when molded plastic hinges are used. That is, due to the nature of the material, the hinging element tends to take on the configuration in which it spends most of its time. For example, if a plastic part is continually forced into some shape by an external source, the plastic part will ultimately take a "set" in that configuration. In the case of base cap 32, button portion 64 is configured to be in its natural or rest position when the hinge element 68 is not bent. However, when depressed to accomplish the reset function of restriction indicator gauge 20, button portion 64 is depressed and hinge element 68 is bent some distance. It would be highly undesirable to have base cap 32 take on a configuration where button element 64 is maintained in its depressed position due to continuous bending of hinge element 68. The present invention however specifically avoids this problem by appropriately configuring locking extension 70, with lock ring 42.

As has previously been described, locking extension 70 is specifically configured to extend through lock ring opening 74. As can be seen in FIG. 4, when restriction indicator gauge 20 is in its reset configuration, locking extension 70 is contained by lock ring opening 74 such that the button portion 64 is retained or held in its rest position at almost all times. This is critical as it avoids any "setting" of the hinge element 68 in an undesired configuration.

Referring now to both FIGS. 5 and 8, indicator cup 38 includes a cylindrical extension 82 which substantially covers locking extension 70. Similarly, housing 30 includes a related substantially cylindrical housing 84 aligned with indicator cup cylindrical extension 82. Both cylindrical extension 82 and cylindrical housing 84 are coaxially aligned with one another such that movement of diaphragm assembly 48 is sufficiently contained within the restriction indicator gauge. This relationship provides proper alignment for diaphragm assembly 48. Referring specifically to FIG. 8, this coaxial alignment can easily be seen.

As previously indicated, the restriction indicator gauge 20 has a visual indication of when a predetermined vacuum signal has been achieved. As shown above, this indication may simply include the existence or non-existence of indicator cup 38 in window 33. Referring now to FIGS. 10–13, an alternative two color visual indication is shown. In this embodiment, window 33 would display a first color when the gauge is in its reset or rest position, while showing a second color once the gauge has reached its set or locked position. During transitional periods, partial viewing of either color could be obtained.

Figure 10:
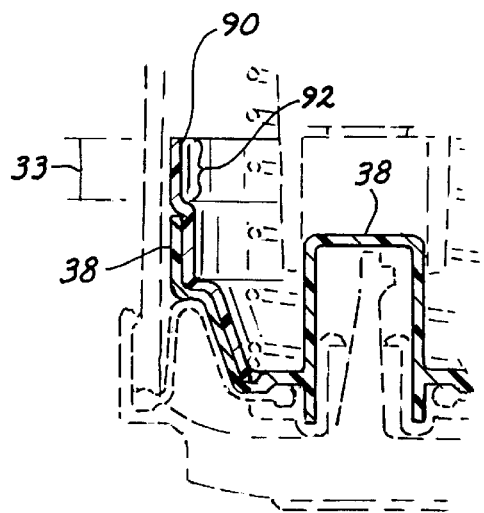
FIGS. 10 and 11 are partial sectional diagrams showing the visual indicator feature in both the reset and set positions respectively.
Figure 11:
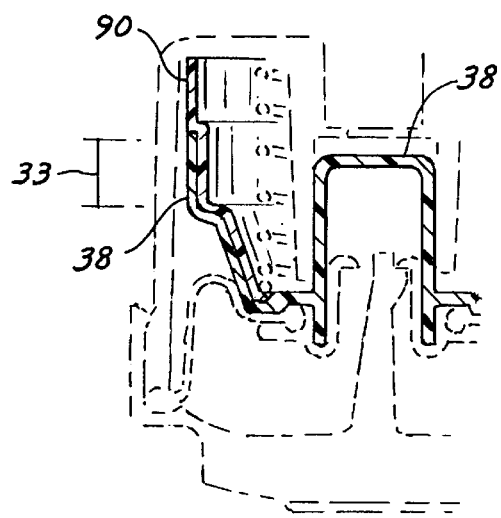

Referring now to FIGS. 10 and 11, there shown one structure for achieving this multicolor display feature. In the device of FIG. 10, the indicator cup 38 has been altered to accommodate a contrasting ring 90 which is seated within the previously existing indicator cup 38. A viewing extension 92 of contrasting ring 90 is specifically configured to extend above the remainder of indicator cup 38.

In this embodiment, housing 30 again has a view window 33 which could be either a clear portion of housing 30 or a clear portion of label 34. In this embodiment, when the gauge is in its reset condition, contrasting ring 90 and specifically viewing extension 92 is positioned immediately adjacent window 33. For example, contrasting ring 90 could be fabricated from a green colored material, consequently a green indication would be shown through window 33. Alternatively, when restriction indicator gauge 20 has reached its set position, both indicator cup 38 and contrasting ring 90 have been moved upwardly. In this set position, the side wall of indicator cup 38 is now positioned immediately adjacent window 33. As indicator cup 38 is colored differently from contrasting ring 90, a different color display will be present in window 33. Consequently, a two color display is achieved by adding contrasting ring 90.

Figure 12:
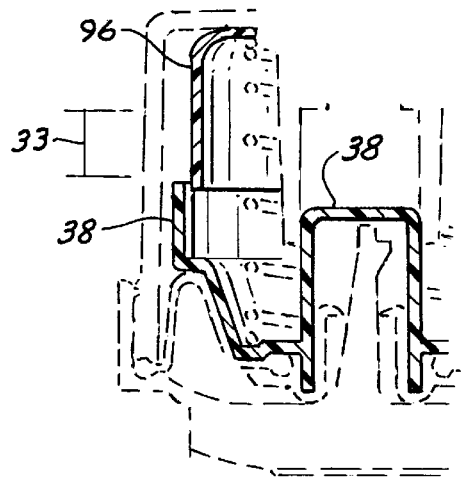
FIGS. 12 and 13 are partial sectional diagrams showing an alternative embodiment of the visual indicator feature in the reset and set positions respectively.
Figure 13:
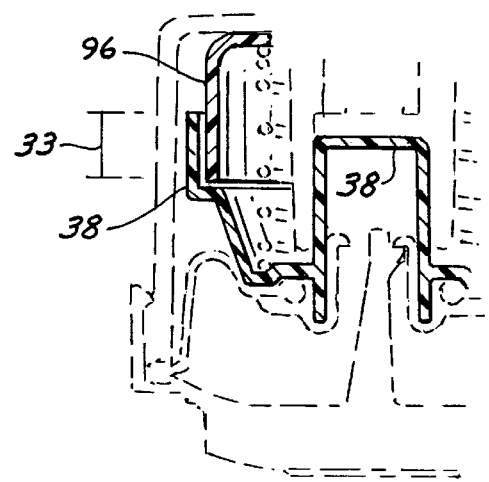

An alternative embodiment for achieving this two color display feature is shown in FIGS. 12 and 13. In this case, an indicator cup 38 substantially similar to that shown in FIGS. 3–5 is used. Additionally, a downwardly extending shield 96 is now attached to an upper portion of housing 30. Generally, shield 96 extends a sufficient distance downward so that it can be viewed through window 33. Consequently, when restriction indicator gauge 30 is in its set position, as shown in FIG. 12, indicator cup 38 will be positioned below window 33 and shield 96 will be exposed. When restriction indicator gauge 20 reaches its set position, however, indicator cup 38 has again been moved to a position immediately adjacent window 33. Thus, indicator cup 38 is now seen through window 33. Again, by fabricating indicator cup 38 and shield 96 from materials of different colors, the contrasting display capability is achieved.

Figure 15:
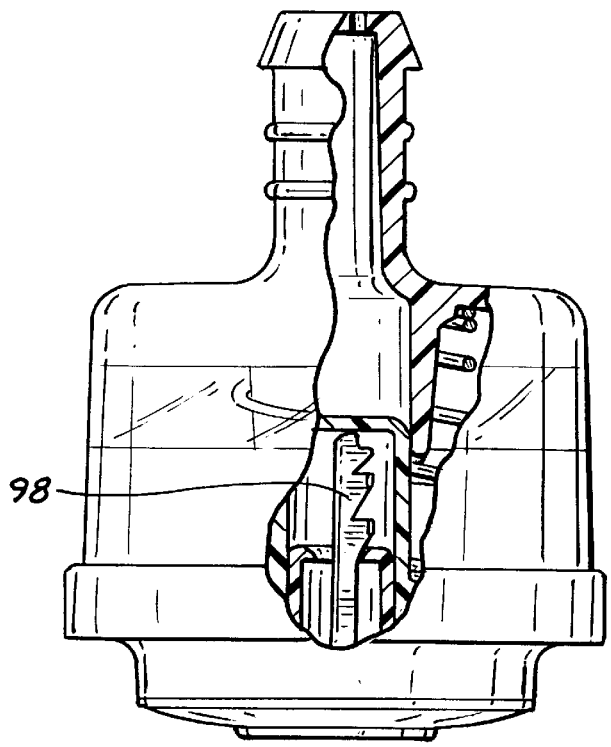
FIG. 15 is a cutaway sectional diagram showing an alternative embodiment of the present invention having multiple locking points and a grommet tip attachment structure.

While the above-described invention has been described as a dual position indicator (either set position or reset position), it is understood that a multi-position gauge could equally be achieved. Referring now to FIG. 15, an alternative locking extension 98 is shown. In this embodiment, multiple locking positions are shown, thus providing the gauge the ability to lock at multiple stages of its operation.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail therein. Rather, reference should be made to the appended claims as indicative of the scope and content of the present invention.

What is claimed is:

1. A low cost air filter restriction indicator gauge attached to an air intake system of an engine to monitor the performance of an air filter, comprising:
    a housing attached to the air intake system having an inlet that communicates a pressure signal between the housing and the air intake system;
    a diaphragm assembly attached to the housing to create an enclosed chamber within the housing which is in communication with the inlet, the diaphragm assembly movable in response to a vacuum signal within the enclosed chamber; and
    a base cap attached to the housing and situated on an opposite side of the diaphragm assembly from the enclosed chamber, the base cap including a reset button integral with said base cap, the reset button having a locking extension integral with said base cap, said base cap bendable at a hinge portion from a rest position in which no bending or flexing is present, to a flexed position in which a recoil force is developed in said hinge portion due to a lateral displacement of said locking extension, said locking extension constructed and arranged to lock the diaphragm assembly in a locked position when the vacuum signal reaches a predetermined level;
    wherein said base cap and said diaphragm are constructed and arranged such that said hinge portion remains in said rest position in an absence of a vacuum signal and when said diaphragm is in said locked position.

2. The low cost air filter restriction indicator gauge of claim 1 wherein the locking extension includes a post with a locking notch at one end which interacts with the diaphragm assembly to lock the diaphragm assembly in a locked position after the vacuum signal reaches the predetermined level.

3. The low cost air filter restriction indicator gauge of claim 1 wherein the diaphragm assembly includes a flexible diaphragm, a lock ring, and an indicator cup.

4. The low cost air filter restriction indicator gauge of claim 3 wherein the locking extension includes a post with a locking notch at one end which interacts with the lock ring to lock the diaphragm assembly in a locked position after the vacuum signal reaches the predetermined level.

5. The low cost air filter restriction indicator gauge of claim 4 wherein the post includes a plurality of locking notches capable of interacting with the lock ring, such that the indicator cup may be locked in multiple positions as the vacuum signal reaches a corresponding set of predetermined levels.

6. The low cost air filter restriction indicator gauge of claim 1 wherein the housing includes a connecting housing groove, and the base cap includes a related connection ridge which cooperates with the groove to form a snap fit connection.

7. The low cost air filter restriction indicator gauge of claim 1 wherein the integral reset button is a circular portion which is surrounded by an annular attachment ring, the integral reset button and annular attachment ring connected via said hinge portion.

8. The low cost air filter restriction indicator gauge of claim 7 wherein the base cap includes a related connection ridge and the housing includes a connecting housing groove, the connection ridge and the housing groove cooperate with one another to form a snap fit connection.

9. The low cost air filter restriction indicator gauge of claim 4 wherein the lock ring includes a centrally located aperture capable of receiving and containing the locking extension therein.

10. The low cost air filter restriction indicator gauge of claim 9 wherein the reset button is depressed to allow the restriction indicator gauge to transition from the set configuration back to the reset configuration.

11. A low cost air filter restriction indicator gauge capable of detecting a filter pressure signal within an air intake system of an engine and providing an indication when the filter pressure signal is above a predetermined level thus suggesting that the air filter needs replacement, the low cost air filter restriction indicator gauge comprising:
    a substantially cylindrical housing attached to the air intake system, the housing having an inlet on one end thereof to receive the filter pressure signal, the housing further having an indicator window located on a cylindrical wall to display that the filter pressure signal has reached a predetermined level;
    a base cap attached to the housing at an end opposite the inlet, the base cap including:
        an annular outer portion, integral with the base cap and attachable to the housing;
        a reset button, integral with the base cap, centrally located within said base cap and surrounded by the annular outer portion, wherein the reset button and the outer portion are integrally connected to one another by a hinge element; and,
        a locking post integral with the reset button which extends toward the housing; and
    a diaphragm assembly including a flexible diaphragm, a lock ring, and an indicator cup, the assembly disposed between the housing and the base cap, the diaphragm assembly forming an enclosed chamber within the housing which is in communication with the inlet, the diaphragm assembly movable in response to a vacuum signal within the enclosed chamber, the diaphragm assembly also configured to cooperate with the locking post to cause the diaphragm assembly to be locked into a set position when the filter pressure signal is above a predetermined level thus providing a visual display through the indicator window;
    wherein the lock ring includes a centrally located aperture for receiving and containing the locking post therein such that the reset button is held in a rest position any time the restriction indicator gauge is in a set or a reset configuration.

12. The low cost air filter restriction indicator gauge of claim 11 wherein the locking post includes a locking notch at one end which interacts with the lock ring to lock the diaphragm assembly in a locked position after the filter signal reaches the predetermined level.

13. The low cost air filter restriction indicator gauge of claim 11 wherein the housing includes a connecting housing groove, and the base cap includes a related connection ridge which cooperate with the groove to form a snap fit connection.

14. The low cost air filter restriction indicator gauge of claim 11 wherein the restriction indicator gauge transitions from the set configuration back to the reset configuration when the reset button is depressed.

15. The low cost air filter restriction indicator gauge of claim 11 wherein the hinge element is maintained in the rest position when the restriction indicator gauge is in the set or the reset configuration.

16. The low cost air filter restriction indicator gauge of claim 11 wherein the indicator cup is visible in the indicator window when the restriction indicator gauge is in said set configuration.

17. The low cost air filter restriction indicator gauge of claim 11 further comprising a contrasting ring attached to the indicator cup such that a viewing extension extends beyond an upper edge of the indicator cup, the viewing extension being visible in the indicator window when the restriction indicator gauge is in said reset configuration while the indicator cup is visible in the indicator window when the restriction indicator gauge is in said set configuration.

* * * * *